(12) United States Patent
Wang et al.

(10) Patent No.: US 10,994,046 B2
(45) Date of Patent: May 4, 2021

(54) HEMOSTATIC MATERIAL, PREPARATION METHOD THEREOF AND PHARMACEUTICAL COMPOSITION CONTAINING THE SAME

(71) Applicant: GENE'E TECH CO., LTD., Taipei (TW)

(72) Inventors: Chung-Hao Wang, Taipei (TW); Shu-Jyuan Yang, Taipei (TW); Li-Cheng Pan, Taipei (TW)

(73) Assignee: GENE'E TECH CO., LTD., New Taipei (TW)

( * ) Notice: Subject to any disclaimer, the term of this patent is extended or adjusted under 35 U.S.C. 154(b) by 0 days.

(21) Appl. No.: 16/250,349

(22) Filed: Jan. 17, 2019

(65) Prior Publication Data
US 2019/0216975 A1 Jul. 18, 2019

Related U.S. Application Data

(60) Provisional application No. 62/619,090, filed on Jan. 18, 2018.

(51) Int. Cl.
| | | |
|---|---|---|
| *A61L 26/00* | (2006.01) | |
| *A61K 38/17* | (2006.01) | |
| *A61K 31/65* | (2006.01) | |
| *A61K 31/635* | (2006.01) | |
| *A61K 31/4439* | (2006.01) | |
| *A61K 31/137* | (2006.01) | |
| *A61K 39/395* | (2006.01) | |
| *A61K 31/728* | (2006.01) | |
| *C07K 16/28* | (2006.01) | |

(52) U.S. Cl.
CPC ........ *A61L 26/0052* (2013.01); *A61K 31/137* (2013.01); *A61K 31/4439* (2013.01); *A61K 31/635* (2013.01); *A61K 31/65* (2013.01); *A61K 31/728* (2013.01); *A61K 38/178* (2013.01); *A61K 38/1709* (2013.01); *A61K 39/3955* (2013.01); *A61K 39/39591* (2013.01); *A61L 26/008* (2013.01); *A61L 26/0023* (2013.01); *A61L 26/0038* (2013.01); *A61L 26/0066* (2013.01); *C07K 16/2839* (2013.01); *A61L 2300/418* (2013.01); *A61L 2300/45* (2013.01); *A61L 2400/04* (2013.01); *A61L 2430/34* (2013.01); *C07K 2317/24* (2013.01)

(58) Field of Classification Search
CPC .................................................. A61L 26/0052
See application file for complete search history.

(56) References Cited

U.S. PATENT DOCUMENTS

| | | | | |
|---|---|---|---|---|
| 4,952,443 | A * | 8/1990 | Gravisse | A01G 9/1438 428/131 |
| 2004/0192658 | A1* | 9/2004 | Hunter | A61K 38/39 514/152 |
| 2007/0009578 | A1* | 1/2007 | Moller | A61L 15/28 424/443 |

* cited by examiner

*Primary Examiner* — Sarah Alawadi
(74) *Attorney, Agent, or Firm* — Rabin & Berdo, P.C.

(57) ABSTRACT

A hemostatic material, a preparation method thereof, and a pharmaceutical composition containing the same are introduced. The hemostatic material includes 200 to 1600 parts by weight of water-insoluble gelatin and 100 to 1000 parts by weight of hydrating material. The preparation method for the hemostatic material includes the steps of (a) providing 200 to 1600 parts by weight of water-insoluble gelatin and 100 to 1000 parts by weight of hydrating material; and (b) combining the water-insoluble gelatin with the hydrating material to form a hemostatic material. The pharmaceutical composition includes an aforementioned hemostatic material and active pharmaceutical ingredients. Through the aforementioned hemostatic material, hemostatic products can increase the blood absorption capacity.

1 Claim, 3 Drawing Sheets

HEMOSTATIC MATERIAL, PREPARATION METHOD THEREOF AND PHARMACEUTICAL COMPOSITION CONTAINING THE SAME

CROSS-REFERENCE TO RELATED APPLICATION

This non-provisional application claims priority under 35 U.S.C. § 119(a) on Patent Application No(s). 62/619,090 filed in U.S. on Jan. 18, 2018, the entire contents of which are hereby incorporated by reference.

FIELD OF THE INVENTION

The present invention relates to a hemostatic material, a preparation method thereof, and a pharmaceutical composition containing the same, especially, a hemostatic material that can increase the blood absorption capacity.

BACKGROUND OF THE INVENTION

When a doctor performs an operation on a patient, if the patient's body part or trauma wound that undergoes surgery is relatively large, excessive bleeding often occurs. When excessive bleeding happens at the patient's body part or trauma wound that undergoes surgery, it will not only affect the physician's visible size of the surgical site during the operation, but also prolong the operation time, thereby increasing the risk of surgical failure. In order to minimize the excessive bleeding condition at the patient's body part or trauma would happening during the operation. Currently, there are many hemostatic products on the market. These hemostatic products are placed in the surgical site or trauma wound during the operation to absorb a large amount of blood; and can prevent and block bleeding in the patient's body part or trauma wound that undergoes surgery, such as hemostatic cotton, hemostatic gel and other hemostatic products.

SUMMARY OF THE INVENTION

Nevertheless, in order to effectively reduce the impact of excessive bleeding on the operation process, how to improve the blood absorption capacity of a hemostatic product remains a problem to be solved.

The objective of the present invention directs to the aforementioned problem and provides a hemostatic material, comprising 200 to 1600 parts by weight of water-insoluble gelatin and 100 to 1000 parts by weight of hydrating material.

For the hemostatic material as described in aforementioned paragraph, the hydrating material is selected from the group consisting of hyaluronic acid, collagen, water-soluble gelatin, glucose and a combination thereof.

For the hemostatic material as described in aforementioned paragraph, the water-insoluble gelatin is Spongostan™ hemostatic cotton.

For the hemostatic material as described in aforementioned paragraph, the water-insoluble gelatin and the hydrating material are combined together to form a graft polymer.

For the hemostatic material as described in aforementioned paragraph, the weight ratio of the water-insoluble gelatin and the hydrating material is 1:2.5.

In order to achieve the aforementioned objective and other objectives, the present invention provides a preparation method of the hemostatic material, comprising the following steps of: (a) providing 200 to 1600 parts by weight of water-insoluble gelatin and 100 to 1000 parts by weight of hydrating material; and (b) combining the water-insoluble gelatin with the hydrating material to form a hemostatic material.

For the preparation method as described in aforementioned paragraph, the water-insoluble gelatin and the hydrating material are combined together by chemical grafting method.

For the preparation method as described in aforementioned paragraph, the weight ratio of the water-insoluble gelatin and the hydrating material is 1:2.5.

In order to achieve the aforementioned objective and other objectives, the present invention provides a pharmaceutical composition containing the aforementioned hemostatic material and pharmaceutical ingredients.

For the pharmaceutical composition as described in aforementioned paragraph, the pharmaceutical ingredients are selected from the group consisting of Minocycline, Celebrex, Rosiglitazone, Fingolimod, Natalizumab, E-selectin and a combination thereof.

By using the hemostatic material as described in aforementioned paragraph, the hemostatic products can increase the blood absorption capacity.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
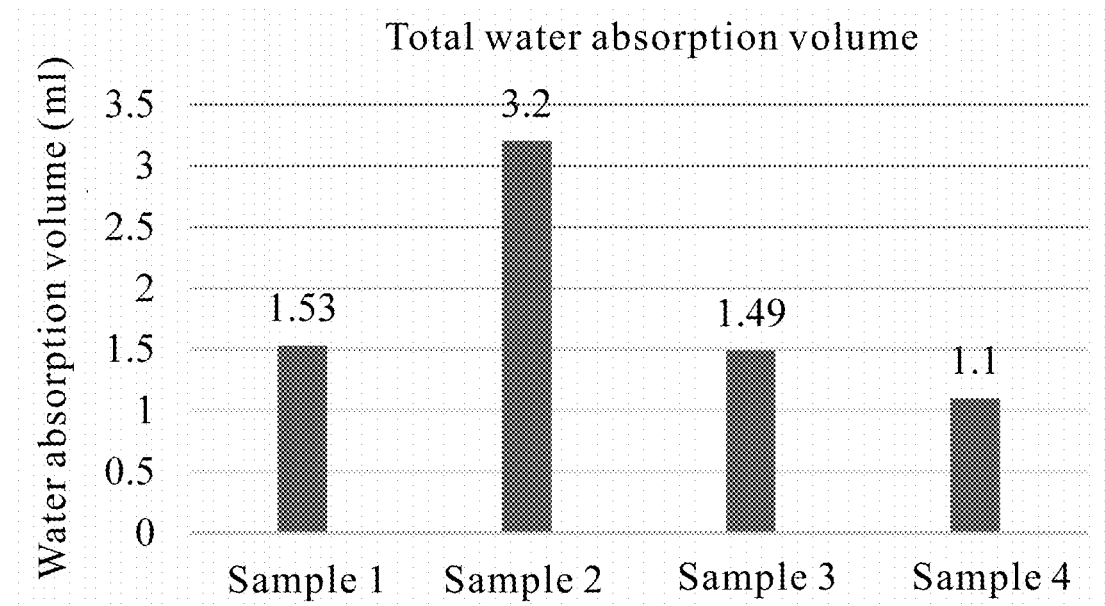
FIG. 1 is a diagram of water absorption capacity test results of the hemostatic material of the embodiment of the present invention in terms of total water absorption volume.

For better understanding the objective, novel features and effect, and advantages of the present invention that can be achieved, detailed descriptions of the present invention are provided as follows, accompanied by diagrams and preferred embodiments.

The preparation method of the hemostatic material:
Prepare 200 to 1600 parts by weight of water-insoluble gelatin and 100 to 1000 parts by weight of hydrating material.

Combine 200 to 1600 parts by weight of water-insoluble gelatin and
100 to 1000 parts by weight of hydrating material to form a hemostatic material. The water-insoluble gelatin and the hydrating material are mixed uniformly in water and undergo a binding reaction or are combined through currently well-known chemical synthesis methods such as a cross-linking reaction and a chemical grafting method.

The water-insoluble gelatin can be acquired from water-insoluble gelatin products available on the market, or obtained from animal tissue (such as pig skin). The water-insoluble gelatin is a biodegradable and absorbable material. Therefore, the water-insoluble gelatin has high biocompatibility. The parts by weight of the water-insoluble gelatin can be 200, 300, 400, 500, 600, 700, 800, 900, 1000, 1100, 1200, 1300, 1400, 1500 or 1600 and, however, the water-insoluble gelatin is not limited to said values described above.

The hydrating material is selected from the group consisting of hyaluronic acid, collagen, gelatin, dextran and a combination thereof. The hydrating materials described in the aforementioned group are all biodegradable and absorbable materials and, therefore, have high biocompatibility. However, in other embodiments, hydrating materials having similar characteristics to those of the hydrating materials in the aforementioned group may be chosen and are not limited to said hydrating materials described in this embodiment. The parts by weight of the hydrating material can be 100, 200, 300, 400, 500, 600, 700, 800, 900 or 1000.

In addition, in order to steadily preserve the hemostatic material, the hemostatic material can be produced in the form of dry cotton pallets through the existing freeze-drying processes.

Preparing samples 1-4 of hemostatic materials: In this embodiment, produce samples 1-4 of hemostatic materials according to the aforementioned preparation method and the specific preparation process is described as follows. Sample 1 is a hemostatic material of the prior art composed of only the water-insoluble gelatin. Therefore, in the following descriptions, sample 2 is used as an example to explain the preparation process of the hemostatic material. The preparation processes of samples 3 and 4 of the hemostatic materials are the same as that of sample 2; the only difference is that the values of parts by weight of the hydrating materials used in the preparation process are different. Furthermore, the composition ratios of the water-insoluble gelatin and the hydrating material used in the preparation process of samples 2, 3 and 4 of the hemostatic materials are disclosed in the following tables.

First, values of parts by weight of the water-insoluble gelatin and the hydrating materials are listed in Table 1. For samples 1-4 of the hemostatic materials of the embodiment, Spongostan™ hemostatic cotton is selected as the water-insoluble gelatin material; the hydrating material of samples 2-4 is hyaluronic acid. However, in other embodiments, other types of hydrating materials and other types of water-insoluble gelatins of aforementioned materials can be chosen to produce the hemostatic material. Last, after the aforementioned hyaluronic acid and the water-insoluble gelatin are mixed uniformly in water, the hyaluronic acid and the water-insoluble gelatin undergo a binding reaction and produce the hemostatic material of sample 2. The preparation processes of samples 3 and 4 are the same as that of sample 2 and, therefore, will not be repeated again.

TABLE 1

Parts by weight of the hemostatic materials of samples 1-4 by ingredient

| | water-insoluble gelatin | hyaluronic acid |
|---|---|---|
| Sample 1 | 200 | 0 |
| Sample 2 | 200 | 500 |
| Sample 3 | 200 | 250 |
| Sample 4 | 200 | 200 | unit: parts by weight

Water Absorption Capacity Test of the Hemostatic Material:

First, produce samples 1-4 of the hemostatic materials using the aforementioned preparation methods. Samples 1-4 then undergo the freeze-drying process to become materials in the form of dry cotton pallets. Take one-fourth (a quarter) parts by weight of samples 1-4 in dry cotton pallet form separately and measure the weights ($W_a$) of samples 1-4 without absorbing water. Next, place samples 1-4 separately into four 100 ml beakers which are filled with 50 ml pure water individually for water absorption tests. Begin timing upon placing samples 1-4 in water; after every one minute duration remove samples 1-4 from water and measure the weights ($W_b$) of samples 1-4 individually after water absorption. Continue the process until the water absorption of samples 1-4 reaches saturation, that is, when the weights ($W_b$) of samples 1-4 after water absorption do not change any more. Subtract $W_a$ from the last measured $W_b$ of samples 1-4 individually to obtain the weights of water absorption of samples 1-4 respectively. The total water absorption capacities of samples 1-4 individually are identified. In addition, divide the total water absorption capacities of samples 1-4 by the water absorption duration time for samples 1-4 to reach saturation respectively thus to obtain the water absorption rates individually.

Figure 2:
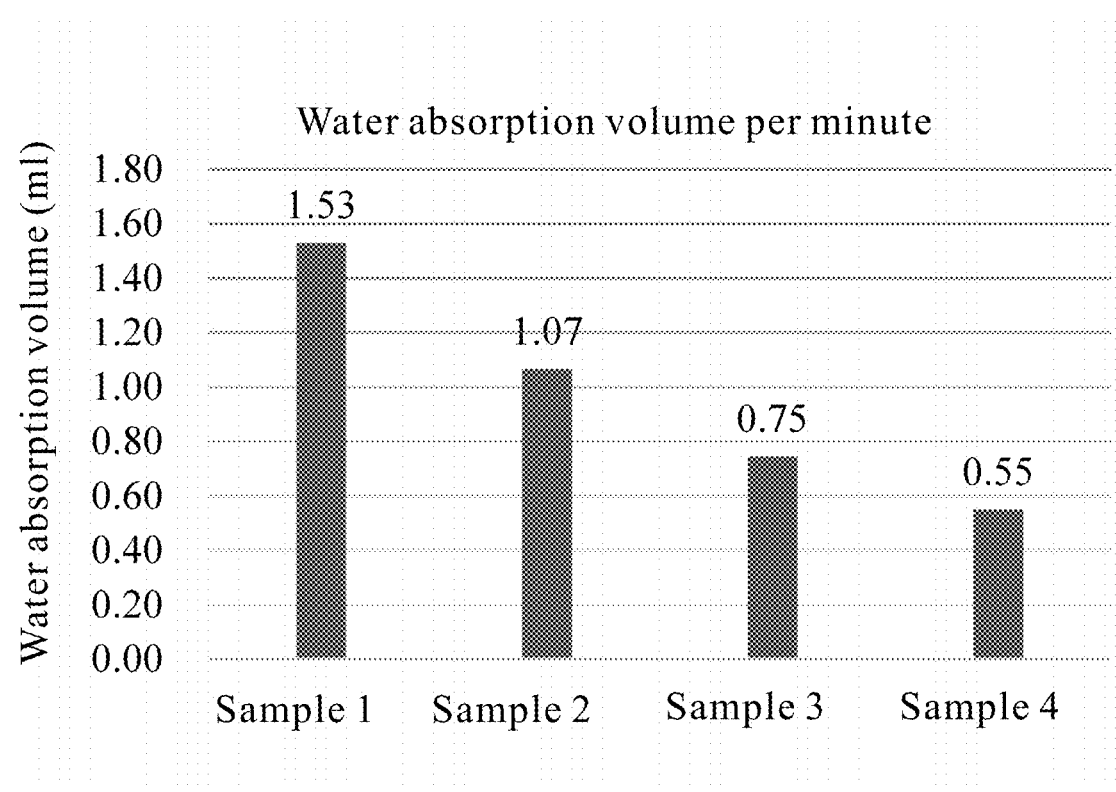
FIG. 2 is a diagram of water absorption capacity test results of the hemostatic material of the embodiment of the present invention in terms of water absorption rate.

FIG. 1 shows the water absorption capacity test results of samples 1-4. According to FIG. 1, sample 2 has the highest water absorption capacity among four samples. FIG. 2 shows the water absorption rates of samples 1-4 (is denoted by water absorption capacity per minute). According to FIG. 2, sample 1 has the highest water absorption rate among four samples; sample 2 has the second highest water absorption rate. In other words, according to these test results, when the water-insoluble gelatin and the hydrating material are combined together with a weight ratio of 1:2.5 to produce the hemostatic material, the hemostatic material has the largest total absorption capacity and a good absorption rate. Based on the tests conducted on the hemostatic material of the embodiment produced by combining the water-insoluble gelatin and the hydrating material, the hemostatic material has the effect of increasing the water absorption capacity. Therefore, the hemostatic material of the embodiment is able to increase the blood absorption capacity than that of hemostatic materials of the prior art (for example, the hemostatic material of the prior art that is composed of only water-insoluble gelatin).

Furthermore, when the hydrating material of the embodiment (such as hyaluronic acid) is combined with the water-insoluable gelatin through the chemical grafting method to produce the hemostatic material of the embodiment, the binding structure created by the combination of water-insoluable gelatin and hydrating material is more tightly packed which will further improve the water absorption rate of the hemostatic material.

Biocompatibility Test of the Hemostatic Material:

First, produce samples 1-4 of the hemostatic materials using the aforementioned preparation methods of the hemostatic materials. Prepare five 6-well cell culture plates at the same time. For each 6-well cell culture plate, fill three wells thereof with 2 ml NIH/3T3 cell culture fluid individually (using DMEM culture fluid for cell culture; the cell density of NIH/3T3 to be $1 \times 10^5$ cells/ml) as cell test samples. NIH/3T3 cells are a type of mouse embryonic fibroblasts (MEF); NIH/3T3 cells are used to test and measure whether the hemostatic material of the embodiment has cytotoxicity or not.

Next, add sample 1 of the hemostatic material to those three cell test samples of the first 6-well cell culture plate as the experimental group 1; the volume ratio of sample 1 of the hemostatic material and the cell culture fluid of each cell test sample is 1:100 respectively. In addition, by applying the same aforementioned method of adding sample 1 of the hemostatic material to three cell test samples in the first 6-well cell culture plate, add samples 2-4 of the hemostatic materials to the second to the fourth 6-well cell culture plates respectively as experimental groups 2-4 respectively. The fifth 6-well cell culture plate is not added with any hemostatic material sample and is used as the control group. Last, place the 6-well cell culture plates of the experimental groups 1-4 and the control group in a cell culture incubator to be kept at 37° C. to promote cell growth. After 24 hours and 48 hours of cell growth, use MTT, 3-(4,5-Dimethylthiazol-2-yl)-2,5-diphenyltetrazolium bromide to perform MTT experiments to test the cell viability of experimental groups 1-4 and the control group. Based on the MTT test results, calculate the average cell viability percentage of experimental groups 1-4 and the control group.

Figure 3:
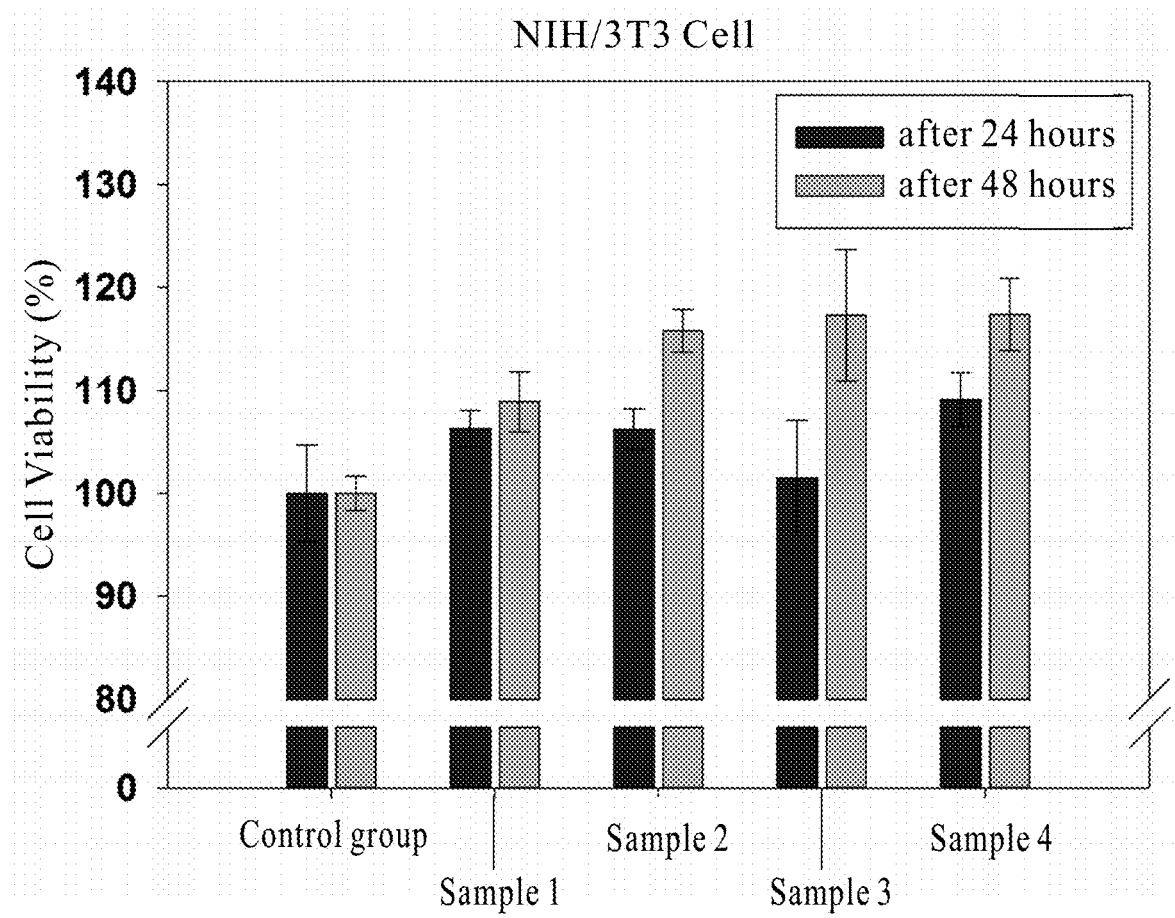
FIG. 3 is a diagram of biocompatibility test results of the hemostatic material of the embodiment of the present invention in terms of cell viability.

FIG. 3 shows the biocompatibility test results of the hemostatic material in terms of cell viability. According to FIG. 3, after 24 hours and 48 hours of cell growth of experimental groups 1-4 that are added with samples 1-4 of the hemostatic material, the numbers of cells of experimental groups 1-4 have increased compared to that of the control group. Therefore, the hemostatic material of the embodiment (such as samples 2-4 of the hemostatic materials) has high degree of biocompatibility and does not have cytotoxicity. In addition, the hemostatic material of the embodiment has better effect on promoting cell growth.

Preparation Method of the Pharmaceutical Composition:

In this embodiment, a pharmaceutical composition containing the aforementioned hemostatic material and pharmaceutical ingredients is further provided and is produced through the following preparation method First, prepare 200 to 1600 parts by weight of water-insoluble gelatin, 100 to 1000 parts by weight of hydrating material, and pharmaceutical ingredients. The preferable parts by weight of the pharmaceutical ingredient is 0.5 to 10 parts by weight. Next, the 200 to 1600 parts by weight of water-insoluble gelatin, the 100 to 1000 parts by weight of hydrating material, and the pharmaceutical ingredients together are mixed uniformly in water and undergo a binding reaction to form the pharmaceutical composition. In this embodiment, the aforementioned preparation method of the hemostatic material can be applied to produce the hemostatic material used in this embodiment; then the hemostatic material and the pharmaceutical ingredients are mixed uniformly in water and undergo a binding reaction to produce the pharmaceutical composition. Furthermore, in this embodiment, the hemostatic material and the pharmaceutical ingredients can also be combined through a chemical modification method (such as a cross-linking reaction, a chemical grafting method) or existing drug encapsulation technologies, or the pharmaceutical ingredients are wrapped within the hemostatic material.

Through the aforementioned method of combining the pharmaceutical ingredients and the hemostatic material, the hemostatic material can deliver and release the drug within the human body eventually. The hemostatic material of the embodiment can be applied not only to stop the bleeding, but also to be a drug carrier. In other words, during the surgical process, the pharmaceutical composition containing the hemostatic material, serving as the drug carrier, can be applied to the area of the patient's wound, so that the pharmaceutical composition can function as to stop the wound from bleeding and to provide drug treatments to the wound at the same time. For example, the pharmaceutical composition of the embodiment can be the combination of a hemostatic material and anti-inflammatory pharmaceutical ingredients. Consequently, the pharmaceutical composition can stop the bleeding of the wound and release the anti-inflammatory drug simultaneously, in order to reduce the probability of an inflammatory reaction from occurring. Furthermore, hyaluronic acid contained in the pharmaceutical composition can effectively increase the total water content, thus to prolong the degradation time for releasing drug from the pharmaceutical composition In addition, in order to steadily preserve the pharmaceutical composition, the pharmaceutical composition can further be produced in the form of dry cotton pallets through the existing freeze-drying processes.

In the embodiment, the pharmaceutical ingredients are an anti-inflammatory drugs and the anti-inflammatory drugs are selected from the group consisting of Minocycline, Celebrex, Rosiglitazone, Fingolimod, Natalizumab, E-selectin and a combination thereof. However, in other embodiments, pharmaceutical ingredients having similar characteristics to those of the anti-inflammatory drugs in the aforementioned group or other pharmaceutical ingredients other than the anti-inflammatory drugs may be chosen and are not limited to said pharmaceutical ingredients described in this embodiment. The parts by weight of the pharmaceutical ingredient can be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10, and the pharmaceutical ingredient is not limited to said values described above.

Tests of Drug Release Rates of the Pharmaceutical Composition:

In this embodiment, produce samples A-D of pharmaceutical compositions according to the aforementioned preparation method of the pharmaceutical composition and the specific preparation process is described as follows. Sample A is produced by having a hemostatic material of the prior art composed of only the water-insoluble gelatin and the pharmaceutical ingredient to be mixed uniformly in water and to undergo a binding reaction. Therefore, in the following descriptions, sample B is used as an example to explain the preparation process of the pharmaceutical composition. The preparation processes of samples C and D of the pharmaceutical compositions are the same as that of sample B; the only difference is that the composition ratios of the hydrating materials used in the preparation process are different. Furthermore, the composition ratios of the water-insoluble gelatin, the hydrating material, and the pharmaceutical ingredients used in the preparation process of samples A-D of the pharmaceutical compositions are disclosed in the following tables.

First, values of parts by weight of the water-insoluble gelatin, the hydrating materials, and the pharmaceutical ingredients are listed in Table 2. For samples A-D of the pharmaceutical compositions of the embodiment, Spongostan™ hemostatic cotton is selected as the water-insoluble gelatin material; the hydrating material of samples B-D is hyaluronic acid; Minocycline is selected as the pharmaceutical ingredient. However, in other embodiments, other types of hydrating material, other types of water-insoluable gelatin, and other pharmaceutical ingredients described in the aforementioned preparation method of the hemostatic material may be chosen to produce the pharmaceutical composition. Last, after the aforementioned hyaluronic acid, the water-insoluble gelatin, and the pharmaceutical ingredient are mixed uniformly in water and undergo a binding reaction and then produce the pharmaceutical composition of sample B. The preparation processes of samples C and D are the same as that of sample B and, therefore, will not be repeated again. After samples A-D of the pharmaceutical compositions are produced, take 3 ml of samples A-D of the pharmaceutical compositions separately and place them into 4 separate dialysis bags

TABLE 2

Parts by weight of the pharmaceutical compositions of samples A-D by ingredient

|  | water-insoluble gelatin | hyaluronic acid | Minocycline |
|---|---|---|---|
| Sample A | 200 | 0 | 1 |
| Sample B | 200 | 500 | 1 |
| Sample C | 200 | 250 | 1 |
| Sample D | 200 | 200 | 1 | unit: parts by weight

Next, prepare four 500 ml beakers and pour 300 ml phosphate buffered saline (PBS) into the beakers separately. Soak aforementioned four separate dialysis bags that contain samples A-D of the pharmaceutical compositions in PBS solution of each beaker separately, and place the aforementioned four beakers that contain the dialysis bags and PBS solution at 37° C. The aforementioned four beakers are rotated at 100 rpm so that the pharmaceutical ingredients inside the dialysis bags located in the beakers can be released into the PBS solution. Retrieve 1 ml of PBS solution from each beaker to analyze the concentration of Minocycline in the PBS solution by high performance liquid chromatography (HPLC) at the specific points of time listed below, that is, to measure the pharmaceutical ingredient content released from the dialysis bags. Besides, when retrieve 1 ml of PBS solution from the PBS solution in the beaker at each specific point of time, at the same time, add 1 ml of fresh PBS solution to each beaker separately. The specific points of time to retrieve the PBS solution are: 0.25, 0.5, 0.75, 1, 1.25, 1.5, 1.75, 2, 2.5, 3, 3.5, 4, 5, 6, 7, 8, 10, and 24 hours.

Figure 4:
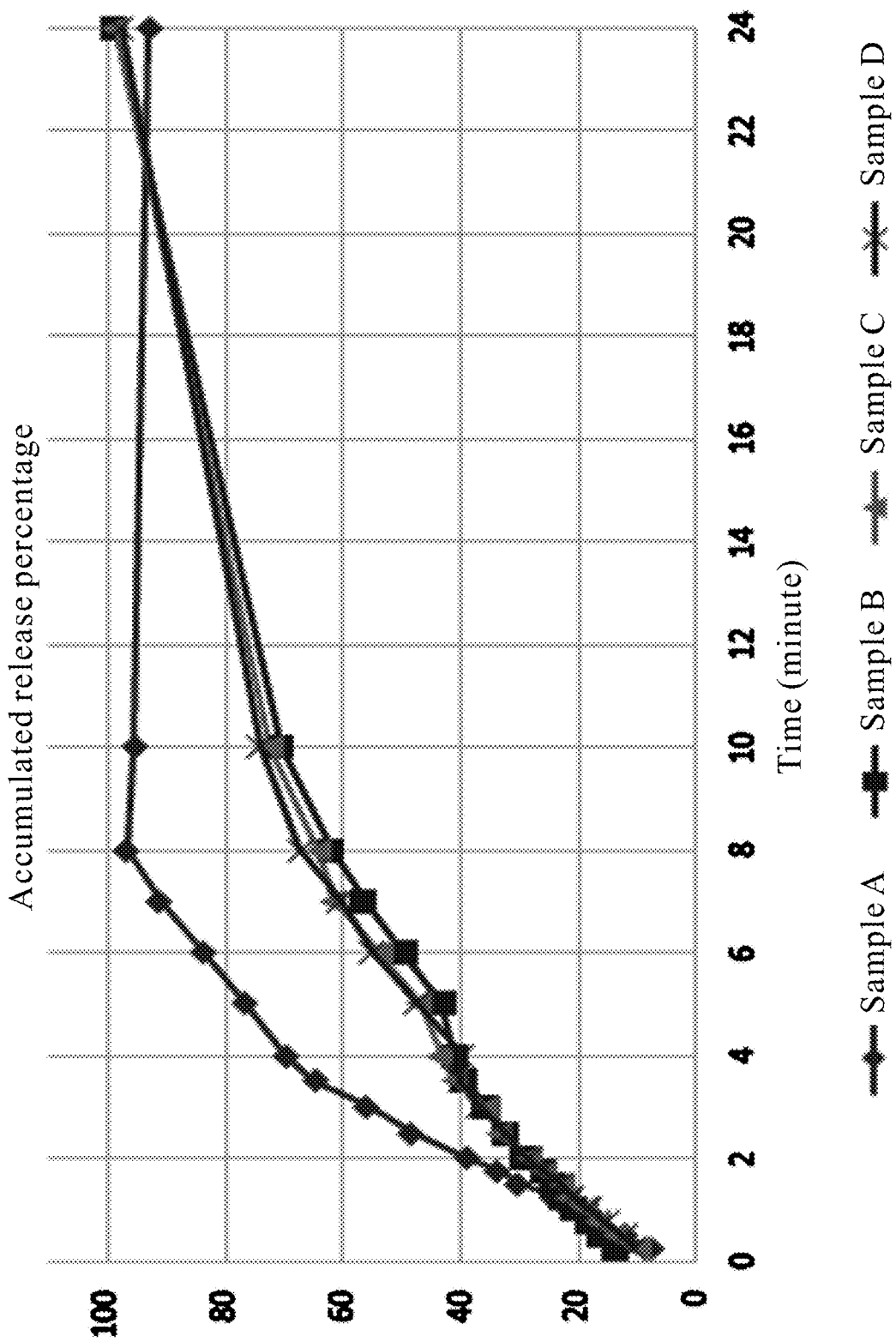
FIG. 4 is a diagram of drug release rates of the pharmaceutical composition of the embodiment of the present invention.

FIG. 4 shows the drug release rates of samples A-D of the pharmaceutical composition. According to FIG. 4, compared to sample A that does not contain hyaluronic acid, all samples B-D to which hyaluronic acid was added have the tendency to release the pharmaceutical ingredient, Minocycline, slowly. The test results in FIG. 4 show that when the hemostatic material of the embodiment is served as a drug carrier, the water-insoluable gelatin and the hydrating material (such as, hyaluronic acid used in samples 2-4 of the hemostatic material and samples B-D of the pharmaceutical composition) provide the effect of prolonging the duration time for releasing drug.

The hemostatic material of the embodiment not only has the effect of increasing the blood absorption capacity, the hemostatic material but also can carry the anti-inflammatory drugs to solve the other problem of the hemostatic material of the prior art.

Currently, during the course of using the hemostatic material of the prior art, due to the ingredients of the hemostatic material, the speed of stopping the bleeding, the degree of adhesion on the surface of the wound, and other factors, the hemostatic material may cause other side effects to the surgical patient, for example, problems of infection at the patient's body parts that undergo the surgery or the wound, foreign-body reaction, granulomatous inflammation, intracranial abscess, or recurrent brain tumor.

In order to solve the inflammatory problems occurring during the course of using the hemostatic material of the prior art, the hemostatic material and the anti-inflammatory drug of the embodiment can be combined in accordance with the aforementioned preparation method of the pharmaceutical composition to produce a hemostatic products with the anti-inflammatory effect. Such hemostatic product can be used during the surgery to reduce the possibility of infecting the patient's body parts or the wound where the surgery is performed. At the same time, the dose and frequency of injecting anti-inflammatory drugs through the intravenous vein can be reduced.

In addition, the hemostatic material of the embodiment can be used to carry the drugs that promote blood coagulation in order to achieve the effect of quickly stop bleeding at the patient's body part that undergoes the surgery.

By combining the water-insoluble gelatin and the hydrating material, the aforementioned hemostatic material not only can increase the blood absorption capacity, but also can be used to carry drugs, which solves the problem of inflammation at the patient's body parts or wound that undergo the surgery. Meanwhile, the pharmaceutical composition produced by combining the hemostatic material and the pharmaceutical ingredients that can serve as a drug carrier, provides the effect of prolonging the duration time for releasing drug and remaining in the human body, thus to increase the reaction time of the drug in the human body.

The above preferred embodiments are presented to disclose the novel features, contents, and advantages of the present invention. Those skilled in the art shall understand that the aforementioned descriptions are for illustration only and shall not be interpreted to limit the scope, applicability or configuration, of the present invention in any way. Any alternative embodiments that are modified or changed without departing from the spirit and scope of the present invention shall be included in the appended claims.

The invention claimed is:

1. A preparation method of a hemostatic material, comprising:
   (a) providing 200 parts by weight of water-insoluble gelatin and 500 parts by weight of hyaluronic acid; and
   (b) combining the water-insoluble gelatin with the hyaluronic acid by mixing uniformly in water to form the hemostatic material.

* * * * *